United States Patent [19]
Miyagi et al.

[11] 4,338,811
[45] Jul. 13, 1982

[54] METHOD AND APPARATUS FOR DIAGNOSIS OF DISEASE

[75] Inventors: Hiroyuki Miyagi, Mito; Yoshinori Takata, Ibaraki; Junkichi Miura, Hitachi; Mamoru Taki, Hitachi, all of Japan

[73] Assignee: Hitachi, Ltd., Tokyo, Japan

[21] Appl. No.: 201,723

[22] Filed: Oct. 29, 1980

[30] Foreign Application Priority Data

Oct. 30, 1979 [JP] Japan .................................. 54-140613

[51] Int. Cl.$^3$ ........................................... G01N 33/50
[52] U.S. Cl. .................................... 73/23.1; 23/230 B; 364/498
[58] Field of Search ............................ 73/23.1, 61.1 C; 364/498, 415; 23/230 B, 232 C; 422/70, 89

[56] References Cited

U.S. PATENT DOCUMENTS 3,860,393 1/1975 Campen, Jr. ......................... 73/23.1

OTHER PUBLICATIONS

D. L. Wallace et al., "Microprocessor-Based Chromatography Data System", *American Laboratory*, vol. 9 No. 1, pp. 67–74, Jan. 1977.

*Primary Examiner*—Stephen A. Kreitman
*Attorney, Agent, or Firm*—Craig and Antonelli

[57] ABSTRACT

A disease diagnostic method and apparatus in which a two-dimensional pattern diagram representing the relation between integrated values of peaks and the retention times in a chromatogram of substances in a body fluid of a subject is obtained to be geographically compared, for disease diagnostic purpose, with a two-dimensional pattern diagram representing the relation between integrated values of peaks and the retention times in a chromatogram obtained through separating and detecting substances in a body fluid of a normal person, and also with two-dimensional pattern diagrams representing the relation between integrated values of peaks and the retention times in chromatograms obtained through separating and detecting substances in a body fluid of abnormal patients classified by diseases.

10 Claims, 10 Drawing Figures

METHOD AND APPARATUS FOR DIAGNOSIS OF DISEASE

BACKGROUND OF THE INVENTION

1. Field of the Invention

This invention relates to a method and apparatus for diagnosing a disease of a subject by analyzing substances contained in body fluids such as urine and blood by means of chromatography and evaluating the results of analysis on the chromatograms thus obtained.

2. Description of the Prior Art

Various disease diagnostic apparatus such as physical measuring apparatus, for example, a roentogenograph and a cardiograph and biochemical analyzers for body fluid components have been used hitherto in addition to medical consultation and examination by a doctor, and a disease of a subject has been diagnosed on the basis of the results of measurement by such diagnostic apparatus. Since the result of measurement by a single diagnostic apparatus does not provide the data required for decisive diagnosis of a disease in many cases, the results of measurement by a plurality of different diagnostic apparatus are combined for the determination of a disease, resulting in complexity of the process of disease diagnosis.

It is known that more than a thousand kinds of substances are contained in a body fluid such as urine or blood, and a disease of a subject can be accurately determined by analyzing as many substances as possible. Chromatographic methods such as liquid chromatography and gas chromatography is suitable for simultaneous analysis of such many kinds of substances in a body fluid. However, it is difficult, as a matter of fact, to utilize so many substances for the determination of a disease when a chromatogram is to be evaluated manually.

A method of diagnosing a disease of a subject by analyzing the amounts of amines and amino acids in urine by means of liquid chromatography, analyzing the amounts of volatile compounds in urine by means of gas chromatography, processing the chromatograms thus obtained and determining a disease by the pattern recognition technique, is reported by A. B. Robinson and L. Pauling in a paper entitled "Techniques of Orthomolecular Diagnosis" in "CLINICAL CHEMISTRY", Vol. 20, No. 8, 1974, pp. 961–965.

In this reported method for disease diagnosis, chromatogram patterns are obtained for each of a group of people with various human diseases and another group of people who apparently are normal but who represent differences in age, sex, diet, physical activity and other factors. When the patterns are found, a calculation is carried out in which each subject is classified according to its correlation with the different patterns. The test for a pattern is carried out by calculating the probability, P, that each substance is systematically different in its value for the two different groups. The disease is determined on the basis of the relation of the number of substances with the maximum value of the probability P.

SUMMARY OF THE INVENTION

It is a primary object of the present invention to provide a disease diagnostic method and apparatus which can easily determine a disease of an individual by the pattern recognition technique on the basis of a two-dimensional pattern diagram obtained by very simple processing of a chromatogram of data of substances contained in his body fluid.

According to the present invention, for attaining the above object, a chromatogram showing individual peaks corresponding to concentrations of substances detected from a body fluid of a subject is obtained by means of chromatography, and the relation between the data of the individual peaks and the retention times of the peaks is illustrated in the form of a two-dimensional pattern diagram. Then, the two-dimensional pattern diagram thus obtained is geographically compared with a two-dimensional pattern diagram obtained from similar data of a normal person and also with two-dimensional pattern diagrams obtained from similar data of abnormal patients classified by diseases, and the results of comparison are examined to diagnose the disease of the subject. The term "data of individual peaks" is used to generally indicate the integrated values of the individual peaks, that is, the areas of the peaks. However, the data may be heights or levels of the individual peaks when the chromatogram obtained by the analysis is ideal from the viewpoint of chromatographic analysis.

DESCRIPTION OF THE PREFERRED EMBODIMENTS

Figure 3A:
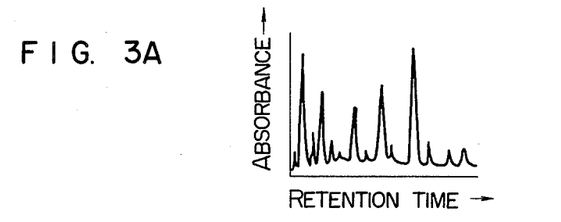
FIGS. 3A, 3B and 3C are diagrams for explaining an example of a two-dimensional pattern diagram used for the disease diagnosis and for diagnosing a disease on the basis of the two-dimensional pattern diagram.
Figure 3B:
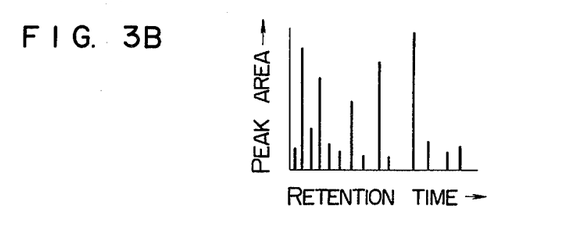
Figure 3C:
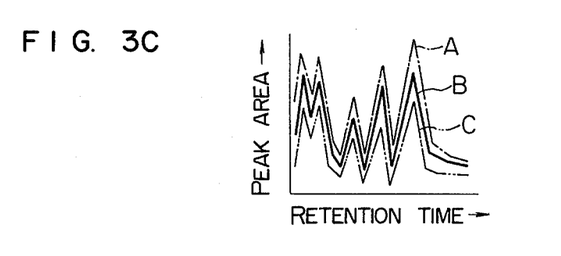

An embodiment of the disease diagnostic method according to the present invention will be described with reference to a flow chart shown in FIG. 1. In this embodiment, substances contained in a body fluid of a subject are separated and detected by means of chromatography such as liquid chromatography or gas chromatography. Peaks of the chromatogram are then individually integrated. Using the data of the chromatogram thus obtained, a two-dimensional pattern diagram representing the relation between the retention times of the individual peaks and the peak areas or integrated peak values is formed. This two-dimensional pattern diagram is, for example, as shown in FIG. 3C described later.

This pattern diagram obtained as the result of the chromatographic analysis of the substances contained in the body fluid of the subject is geographically compared with similar two-dimensional pattern diagrams showing the upper and lower limits respectively of data of normal persons and stored previously in a file, so as to find whether the data of the subject lie within the range of the data of normal persons. It is apparent that the data of normal persons include the upper and lower limits of integrated values and the retention times of individual peaks on the chromatograms obtained through separation and detection of substances in their body fluid. Thus, the pattern diagrams of the normal persons show also the relation between the peak areas and the retention times. When the result of comparison proves that the data of the subject lie within the range of the data of the normal persons, the subject is determined not to be abnormal, and the result is displayed and/or recorded to cease the process of disease diagnosis.

On the other hand, when one or more of the data do not lie within the range of the data of the normal persons, the subject is determined to be abnormal and data corresponding to predetermined items of retrieval described later are retrieved from a previously prepared file of data classified by diseases, and on the basis of such retrieved data, two-dimensional pattern diagrams of diseases are formed. These pattern diagrams are then compared with that of the subject to select a corresponding disease or an analogous disease to the abnormality of the subject. The data classified by diseases above described include similarly the upper and lower limits of integrated values and the retention times of individual peaks on chromatograms obtained through separation and detection of substances contained in body fluids of abnormal patients classified by diseases. Thus, each of the pattern diagrams of diseases shows also the relation between the peak areas and the retention times. The data classified by diseases also include the mean values of the integrated values of the individual peaks, and such mean values are utilized for the calculation of the correlation coefficients described later. When the corresponding disease or analogous disease is selected, a signal indicative of the name of the disease is generated, and the correlation coefficient showing the correlation between the data of the selected disease and the data of the subject is calculated. The result of judgment indicating the possibility of abnormality, the result of selection of the disease and the result of calculation of the correlation coefficient are displayed and/or recorded to complete the process of disease diagnosis.

Figure 2A:
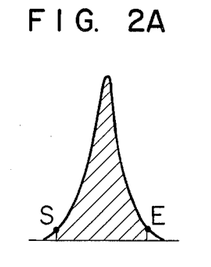
FIGS. 2A and 2B illustrate manners of integrating each individual peak in a chromatogram.
Figure 2B:
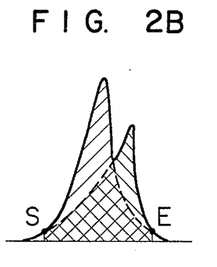

A peak appearing on a chromatogram is integrated in a manner as, for example, shown in FIG. 2A. A preset slope sensitivity ($\mu$V/min) is taken as a reference, and a point S at which the peak rises with a positive gradient larger than the preset slope sensitivity is selected as an integration starting point, while another point E at which the peak has a negative gradient smaller than the reference is selected as an integration ending point. The area of the hatched portion is thus calculated. When a plurality of peaks partly overlap each other or there are so-called shoulder peaks as shown in FIG. 2B, the peaks are separated by tangential division lines as shown by the dotted curves so as to be individually integrated.

The heights or levels of the individual peaks themselves are not used, but the integrated areas of the individual peaks are used as the data for the diagnosis of a disease. This is because proper selection of a reference level of the peaks becomes a problem when the peaks are very close to each other as, for example, shown in FIG. 2B, and also the peak area does not change, but the peak height or level will change, when the retention time of the peak is subject to a variation. Thus, the use of the peak area is for the proper diagnosis of a disease. However, when the chromatogram is obtained in its ideal form, the peak heights or levels themselves may be used as the data for the disease diagnosis, and a two-dimensional pattern diagram showing the relation between the peak heights or levels and the retention times may be formed to be used for the disease diagnosis. In such a case, the data of normal persons and the data of abnormal patients classified by diseases must also be prepared to include the peak heights and the retention times.

The two-dimensional pattern diagrams above described and the process of disease diagnosis on the basis of comparison between them will be described in further detail with reference to FIGS. 3A to 3C. FIGS. 3A to 3C illustrate the process of disease diagnosis in which an anion-exchanger liquid chromatograph provided with a so-called UV-Visible absorption detector is used to analyze substances in urine of a subject to obtain a chromatogram as shown in FIG. 3A, and a disease is diagnosed on the basis of the chromatogram. The relation between the absorbance and the retention time of each of the individual peaks are readily seen from the chromatogram shown in FIG. 3A. However, due to the fact that the substances have different absorption coefficients, the difference between the peak areas or peak levels does not directly reflect the difference between the concentrations of the substances. For the purpose of conversion of a peak area or a peak level on a chromatogram into a concentration, a calibration graph is generally prepared to find the concentration corresponding to the peak area. However, in the case of a sample such as a body fluid containing an extremely large number of substances, it is difficult to prepare such calibration graphs for all of the detected substances.

In the present invention in which a chromatogram pattern is utilized for the diagnosis of a disease, there is utterly no need for converting the individual peaks into the concentrations. More precisely, the levels of the individual peaks can be used as the data for the disease diagnosis when the chromatogram is obtained in an ideal form, as described hereinbefore. Therefore, the tops of the peaks on the chromatogram are successively connected by straight lines to provide a two-dimensional pattern diagram representing the relation between the peak levels and the retention times. When, on the other hand, the chromatogram of ideal form is not obtained, the tops of the bars in the graph shown in FIG. 3B plotting the relation between the areas of the peaks and the retention times of the peaks are connected by lines thereby drawing a two-dimensional pattern diagram as shown by the curve B in FIG. 3C representing the relation between the peak areas and the retention times. Disease diagnosis is carried out on the basis of such a pattern diagram. In the course of preparing such a pattern diagram, a coefficient taking into account the importance of each individual peak or each substance in relation to the disease diagnosis may be used to modify the peak level or the peak area.

The area of each of the peaks is generally calculated for the proper diagnosis of a disease of a subject, and such a process of disease diagnosis will be described with reference to FIG. 3C. The pattern diagram (the curve B shown in FIG. 3C) obtained on the basis of the data of the subject is compared geographically with similar pattern diagrams obtained on the basis of previously filed data of normal persons. The curve A shown in FIG. 3C represents a pattern diagram indicating the upper limits of the data of the normal persons, and the curve C in FIG. 3C represents a pattern diagram indicating the lower limits of the data of the normal persons.

Figure 1:
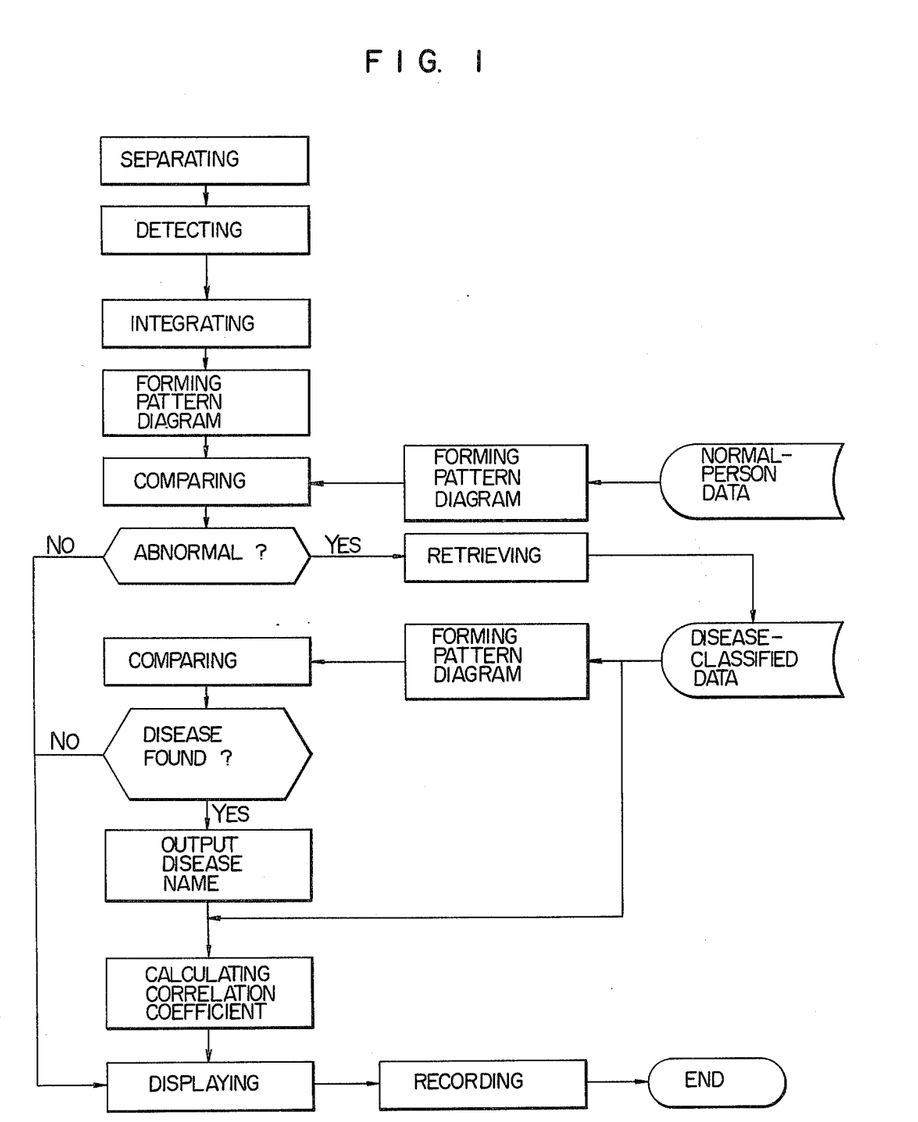
FIG. 1 is a flow chart of an embodiment of the disease diagnostic method according to the present invention.

The subject is diagnosed to be normal or disease-free when the pattern diagram B of the data of the subject lies between the pattern diagrams A and C of the upper and lower limits respectively of the normal persons as shown in FIG. 3C, and the signal indicative of the result of diagnosis is generated to complete the process of disease diagnosis (FIG. 1). The result of diagnosis is displayed on a display unit described later and is also recorded by a hard copy unit which produces a hard copy on which the result of diagnosis is recorded.

When, on the other hand, a portion of the pattern diagram B of the data of the subject deviates even slightly from the range of the data of the normal persons, the subject is diagnosed to be abnormal (FIG. 1). In such a case, the rate of the area of the deviated portion, encircled by the curve B and the curve A or C to the area of that portion between the curves A and C which correspond to the deviated portion is calculated to detect the degree of abnormality.

Such a geographical comparison may be effected, for example, by dividing the diagram of FIG. 3C into a plurality of small areas as usually carried out in the pattern recognition technique. Namely, the abscissa and the ordinate of FIG. 3C are divided into a plurality of small regions to define the small areas in FIG. 3C, and an inspection is made as to whether a point on the curve B and/or a point on the curve A or C is present in each of the small areas.

When the subject is diagnosed to be abnormal, corresponding data or analogous data are retrieved from a previously prepared file of various diseases in accordance with predetermined items of retrieval. The retrieving items are determined in accordance with the relation between the range of retention time of each of the deviated portions and the degree of adnormality of that portion, or the relation between the retention time and the peak area abnormality of each of the abnormal peaks corresponding to the deviated portions. The peak area abnormality designates the rate of the difference between the peak area b of the subject and the upper limit peak area a or lower limit peak area c of the normal persons to the average value of a and c.

The file of diseases lists the data of the upper and lower limits classified by diseases as described hereinbefore, and on the basis of the retrieved data, two-dimensional pattern diagrams of the upper and lower limits of a disease representing the peak areas and the retention times are prepared. These pattern diagrams are geographically compared with that of the subject in a manner similar to that shown in FIG. 3C so as to select one or more corresponding or analogous disease.

After the selection of the disease or diseases, the correlation coefficient between the average-value curve of the selected disease or diseases and the pattern diagram of the subject is calculated so as to obtain the probability of disease diagnosis for the purpose of proper diagnosis of the disease. That is, when one corresponding or analogous disease is selected, the subject is immediately diagnosed to suffer from that disease, while when a plurality of diseases are selected, one or some of them is determined by calculation of the correlation coefficient. The correlation coefficient may be calculated on the basis of the relation between error matrix and covariance.

The result of judgment of the possibility of abnormality, the result of selection of the disease and the result of calculation of the correlation coefficient are displayed on the display unit and recorded by the hard copy unit. In addition to the display and recording of these results of diagnosis, the process of disease diagnosis including the judgment of the possibility of abnormality by comparison between the pattern diagram of the subject and those of the normal persons and also the selection of the disease by comparison between the pattern diagram of the subject and those prepared as the result of data retrieval from the file of data classified by diseases, can also be displayed so that the process of diagnosis of the disease can be clarified. It will be apparent that the step of "integration" (calculation of peak areas) shown in FIG. 1 is unnecessary when the relation between the peak levels and the retention times is used as the data for disease diagnosis.

Figure 4:
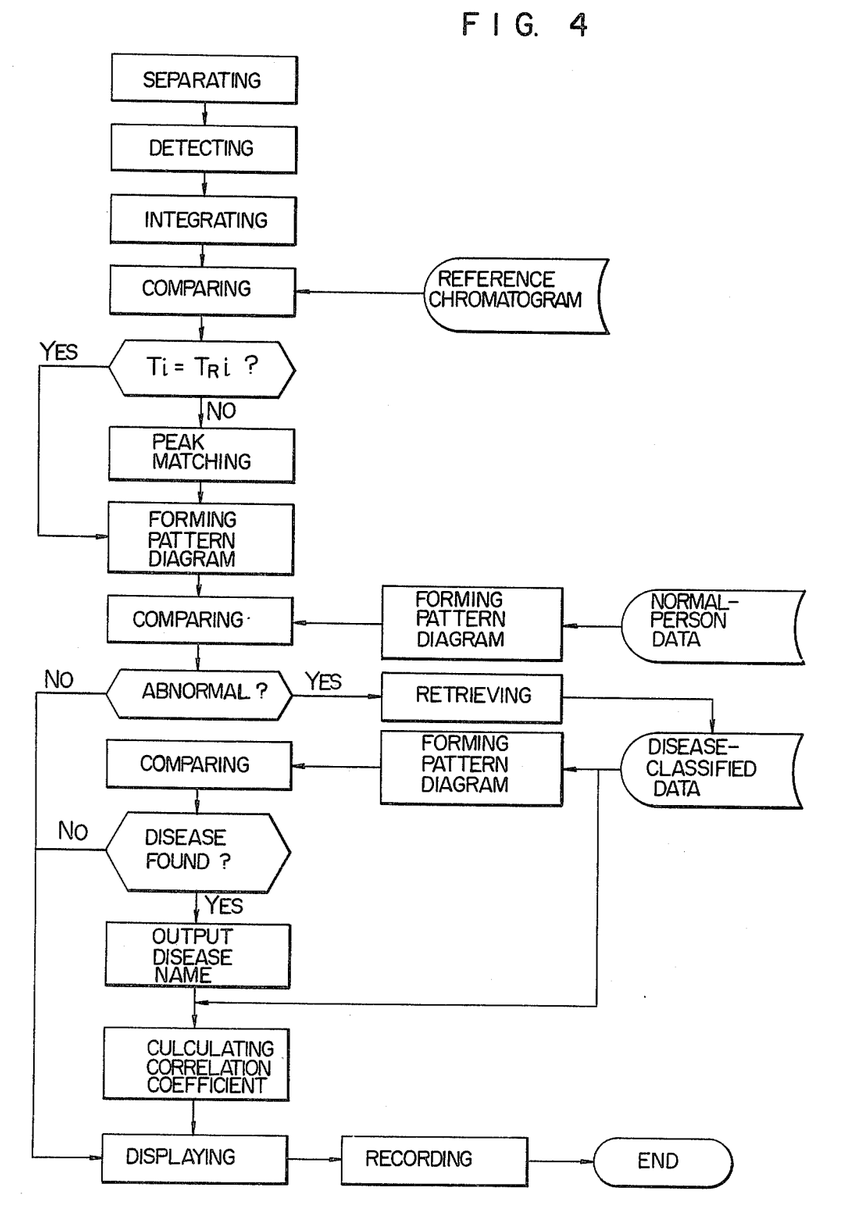
FIG. 4 is a flow chart of another embodiment of the disease diagnostic method according to the present invention.

FIG. 4 is a flow chart showing another embodiment of the method of disease diagnosis according to the present invention. In this embodiment, a chromatogram of a body fluid such as urine of a subject is compared with a reference chromatogram of chemically control urine, and so-called peak matching for eliminating deviation of the position of a peak in the chromatogram of the subject is carried out, so that the retention time $T_i$ of the peak in the subject's chromatogram matches with the retention time $T_{Ri}$ of the corresponding peak in the reference chromatogram. By carrying out such peak matching, system errors such as systematic chromatographic errors and analysis errors can be eliminated. For discriminating the peak position, when a light absorption detector is used, the ratio between the absorbances detected at multiple wavelengths, or the ratio between the sensitivities of two kinds of such detectors can be used for peak identification.

Figure 5:
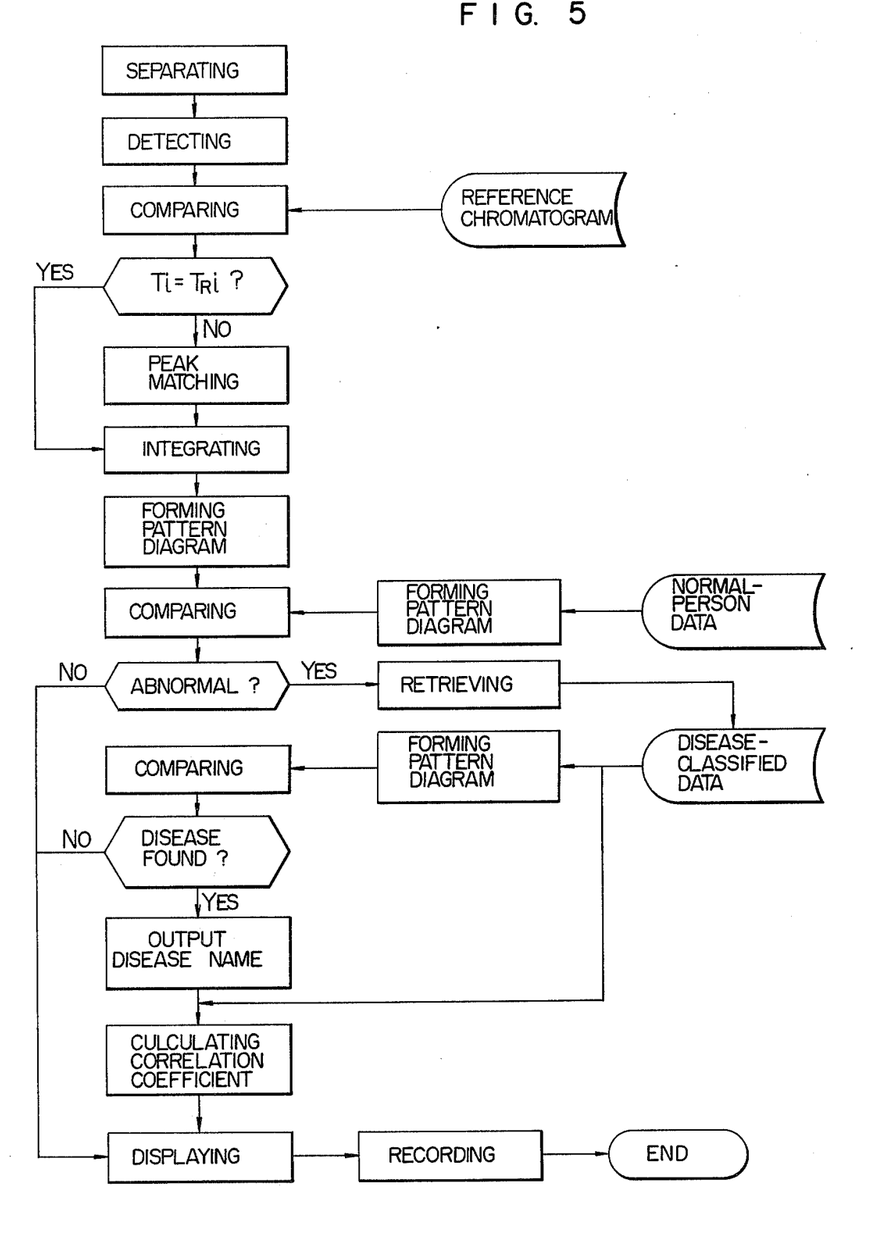
FIG. 5 is a flow chart of still another embodiment of the disease diagnostic method according to the present invention.

This second embodiment is generally similar to the first embodiment shown in FIG. 1 except the step of peak matching. Further, in this second embodiment, whether or not the retention time of each peak in the subject's chromatogram coincides with the retention time of the corresponding peak in the reference chromatogram is judged after the integration of each peak, and the peak matching is carried out when no coincidence is found therebetween. However, the effect of disease diagnosis is entirely the same when the coincidence between the retention times is judged and the peak matching is carried out before the integration, as shown in FIG. 5 which shows another embodiment of the method of disease diagnosis according to the present invention. The difference between the embodiment shown in FIG. 4 and that shown in FIG. 5 is due to the difference in the structure of the disease diagnostic apparatus.

Figure 6:
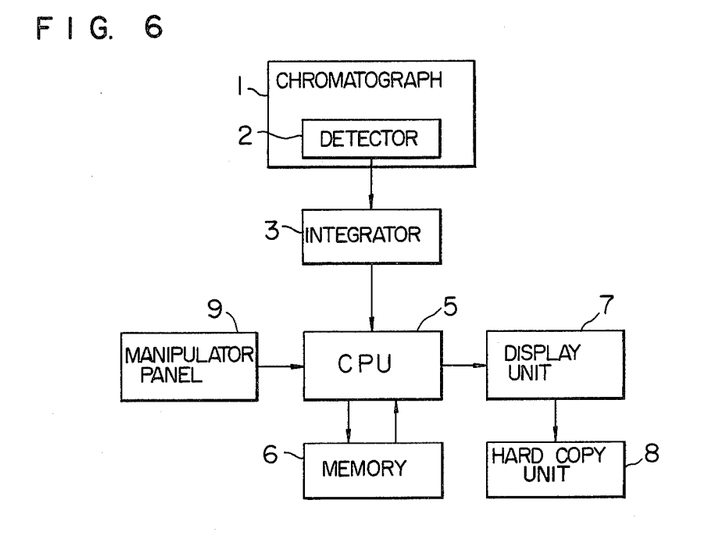
FIG. 6 is a block diagram of an embodiment of the disease diagnostic apparatus according to the present invention adapted for the practice of the methods shown in FIGS. 1 and 4.

FIG. 6 shows the structure of an embodiment of the apparatus adapted for the practice of the method of disease diagnosis shown in FIGS. 1 and 4. Referring to FIG. 6, substances in a body fluid of a subject are separated in a chromatograph 1 to be detected by a detector 2 in the chromatograph 1. Individual peaks in the output signal from the detector 2 are integrated in an integrator 3, and the output signal from the integrator 3 is applied to a central processing unit 5 which is referred to as a CPU hereinafter. In the CPU 5, a two-dimensional pattern diagram representing the relation between the peak areas and the retention times provided by the input signal is formed according to a preset program. When peak matching (shown in FIG. 4) is required, a reference chromatogram is read out from a memory 6 such as a magnetic tape or a magnetic disk, and the two-dimensional pattern diagram above described is formed after the CPU 5 judges whether or not the retention time of each peak in the subject's chromatogram coincides with the retention time of the corresponding peak in the reference chromatogram and carries out peak matching when coincidence is not detected.

Then, the data of the upper and lower limits of normal persons are read out from the memory 6 to form the upper limit pattern diagram and lower limit pattern diagram of the normal persons in the CPU 5. The pattern diagram of the data of the subject is then compared geographically with these upper and lower limit pattern diagrams in the CPU 5 so as to judge whether the subject is normal or abnormal. The result of judgment is displayed on a display unit 7 and recorded by a hard copy unit 8. As described hereinbefore, the process of the comparison and judgment may be displayed when so desired.

The process of disease diagnosis is completed when the subject is judged to be normal. When, on the other hand, the subject is judged to be abnormal, the CPU 5 retrieves disease data in a manner as described hereinbefore from the file of classified diseases stored in the memory 6. On the basis of the thus retrieved disease data, the CPU 5 forms the upper limit pattern diagram and lower limit pattern diagram of the disease and compares geographically these pattern diagrams with the subject's pattern diagram so as to select the corresponding disease or analogous disease. Further, the CPU 5 calculates the correlation coefficient between the pattern diagram of the subject and the average-value curve of the selected disease. The result of selection of the corresponding disease or analogous disease, the result of calculation of the correlation coefficient and/or the process of disease diagnosis by comparison of the pattern diagrams, when so desired, are displayed on the display unit 7 and recorded by the hard copy unit 8. When it is necessary to modify some of the data on the basis of doctor's other observations in the course of judgment of the normality or abnormality or in the course of disease selection, necessary data are applied from a manipulator panel 9 to the CPU 5 for the purpose of modification of the data.

Figure 7:
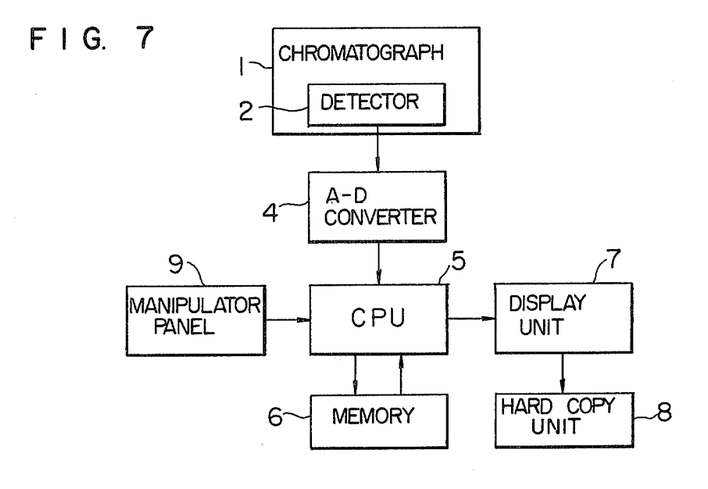
FIG. 7 is a block diagram of another embodiment of the disease diagnostic apparatus according to the present invention adapted for the practice of the methods shown in FIGS. 1 and 5.

FIG. 7 shows the structure of another embodiment of the apparatus adapted for the practice of the method of disease diagnosis shown in FIGS. 1 and 5. The apparatus shown in FIG. 7 is substantially the same so that shown in FIG. 6 except that the integrator 3 shown in FIG. 6 is replaced by an A-D converter 4, and the output signal from the detector 2 is applied through this A-D converter 4 to the CPU 5 so that, after the step of peak matching, each peak is integrated in the CPU 5. It has however been clarified that the provision of the integrator 3 is more advantageous than the provision of the A-D converter 4 since the integration of each peak in the CPU 5 results in a complex program and in an extended length of time required for data processing.

The effectiveness of the present invention was confirmed by a test in which the apparatus shown in FIG. 6 or 7 was used to analyze ultraviolet absorbing substances in urine of a subject by means of anion-exchanger liquid chromatography and to diagnose a disease on the basis of a chromatogram thus obtained.

Employment of the step of peak matching shown in FIG. 3 is effective for the disease diagnosis by the liquid chromatography since this type of chromatography tends to be subject to secular variations of the retention time due to contamination on to the column packings and also due to variations of the resistance of the fluid.

The present invention, in which the combination of the integrated values and the retention times of the peaks are used as the data for judging the presence or absence of abnormality, is advantageous in that the retention time for an abnormal substance can be used as an element of data for determining the retrieving items in the selection of a disease thereby capable of shortening the length of times required for the data retrieval.

The present invention is equally effectively applicable to various disease diagnostic apparatus utilizing various kinds of chromatography including gas chromatography used for the analysis of volatile compounds in urine, gel permeation chromatography used for the analysis of protein and thin-layer chromatography.

The displayed and/or recorded data for disease diagnosis according to the present invention are relatively simple so that the result of the automatic disease diagnosis can be easily examined in its propriety by an examiner or a doctor who diagnoses a disease of a subject.

We claim:

1. A method of diagnosing a disease of a subject by analyzing substances of a body fluid of the subject by means of chromatography and examining a chromatogram thus obtained, the method comprising the steps of:

separating and detecting the substances in the body fluid of the subject to obtain a chromatogram including peaks corresponding to the individual substances;

integrating the individual peaks in the chromatogram of the subject;

forming a two-dimensional pattern diagram representing the relation between the integrated values of the peaks and the retention times in the chromatogram of the subject;

forming a two-dimensional upper limit pattern diagram and a lower limit pattern diagram relating to normal persons on the basis of previously stored data of the upper and lower limits of integrated values of peaks and the retention times in chromatograms obtained by separating and detecting the substances in a body fluid of normal persons;

judging the possibility of abnormality by comparing geographically the pattern diagram of the subject with the upper limit and lower limit pattern diagrams of the normal persons;

retrieving, when the result of judgment proves that the subject is abnormal, data corresponding to predetermined items of retrieval from a previously prepared file of data classified by diseases, said disease-classified data including upper and lower limits and mean values of integrated values of peaks and retention times in chromatograms obtained through separating and detecting substances of a body fluid of abnormal patients classified by diseases;

forming two-dimensional upper limit pattern diagrams and two-dimensional lower limit pattern diagrams of diseases on the basis of the upper and lower limits of the integrated values of peaks and the retention times in the retrieved data; and selecting at least one disease having the pattern diagrams at least analogous to the pattern diagram of the subject by comparing geographically the pattern diagram of the subject with the upper limit and lower limit pattern diagrams of diseases.

2. A method of disease diagnosis as claimed in claim 1, further comprising, between the step of separating and detecting the substances and the step of forming the pattern diagram of the subject, the step of peak matching for matching the retention time of a peak in the chromatogram of the subject with the retention time of the corresponding peak in a previously prepared reference chromatogram.

3. A method of disease diagnosis as claimed in claim 1, further comprising, after the step of selecting the disease, the step of calculating the correlation coefficient between the average-value curve of the selected disease and the pattern diagram of the subject on the basis of the mean values of the integrated value of peaks in the data of the selected disease and the integrated values of peaks in the pattern diagram of the subject.

4. A method of disease diagnosis as claimed in claim 3, further comprising the step of displaying the process and result of judgment of the possibility of abnormality, the step of displaying the process and result of selection of the disease, and the step of displaying the result of calculation of the correlation coefficient.

5. A method of disease diagnosis as claimed in claim 4, further comprising the step of recording the result of judgment of the possibility of abnormality, the step of recording the result of selection of the disease and the step of recording the result of calculation of the correlation coefficient.

6. An apparatus for diagnosing a disease comprising:
detecting means for separating and detecting substances in a body fluid of a subject to generate a signal representing a chromatogram including peaks corresponding to the individual substances;
means for integrating the individual peaks in the output signal generated from said detecting means;
means for forming a two-dimensional pattern diagram representing the relation between the integrated values of the peaks and the retention times in the chromatogram of the subject;
memory means for storing data of normal persons including the upper and lower limits of integrated values of peaks and the retention times in chromatograms obtained through separating and detecting substances in a body fluid of normal persons;
means for forming a two-dimensional upper limit pattern diagram and a two-dimensional lower limit pattern diagram relating to normal persons on the basis of the upper and lower limits of integrated values of peaks and the retention times stored in said memory means;
means for judging the possibility of abnormality by comparing geographically the pattern diagram of the subject with the upper and lower limit pattern diagrams of the normal persons;
memory means for storing data classified by diseases, said disease-classified data including the upper and lower limits and mean values of integrated values of peaks and the retention times in chromatograms obtained through separating and detecting substances in a body fluid of abnormal patients classified by diseases;
means for retrieving data corresponding to predetermined items of retrieval from said stored data classified by diseases;
means for forming two-dimensional upper limit pattern diagrams and two-dimensional lower limit pattern diagrams of diseases on the basis of the upper and lower limits of the integrated values of peaks and the retention times in the retrieved data; and
means for comparing geographically the pattern diagram of the subject with the upper limit and lower limit pattern diagrams of diseases so as to select at least one disease having the pattern diagrams at least analogous to the pattern diagram of the subject.

7. A disease diagnostic apparatus as claimed in claim 6, further comprising memory means for storing data of a reference chromatogram, and means operative in response to the application of the output signal from said detecting means and in response to the application of the data of the reference chromatogram from said memory means for carrying out peak matching for maching the retention time of a peak in the chromatogram of the subject with the retention time of the corresponding peak in the reference chromatogram.

8. A disease diagnostic apparatus as claimed in claim 6, further comprising means for calculating the correlation coefficient between the average-value curve of the selected disease and the pattern diagram of the subject on the basis of the mean values of the integrated values of peaks in the data of the selected disease and the integrated values of peaks in the pattern diagram of the subject.

9. A disease diagnostic apparatus as claimed in claim 8, further comprising means for displaying the process and result of judgment of the possibility of abnormality, the process and result of selection of the disease and the result of calculation of the correlation coefficient.

10. A disease diagnostic apparatus as claimed in claim 9, further comprising means for recording the result of judgment of the possibility of abnormality, the result of selection of the disease and the result of calculation of the correlation coefficient.

* * * * *